US006365204B1

(12) United States Patent
Spendler et al.

(10) Patent No.: US 6,365,204 B1
(45) Date of Patent: Apr. 2, 2002

(54) PREPARATION OF DOUGH AND BAKED PRODUCTS

(75) Inventors: Tina Spendler, Herlev (DK); Lone Nilsson, Binningen (CH); Claus Crone Fuglsang, Niva (DK)

(73) Assignee: Novozymes, Bagsvaerd (DK)

( * ) Notice: Subject to any disclaimer, the term of this patent is extended or adjusted under 35 U.S.C. 154(b) by 0 days.

(21) Appl. No.: 09/286,037

(22) Filed: Apr. 5, 1999

Related U.S. Application Data

(60) Provisional application No. 60/083,277, filed on Apr. 28, 1998.

(30) Foreign Application Priority Data

Apr. 20, 1998 (DK) ................................................ 0543/98

(51) Int. Cl.$^7$ ................................................ A23L 1/10
(52) U.S. Cl. ............................ 426/28; 426/18; 426/19; 426/20; 426/549
(58) Field of Search ........................... 426/549, 18, 19, 426/20, 27, 28, 33, 44

(56) References Cited

U.S. PATENT DOCUMENTS 4,567,046 A    1/1986    Inoue et al.
4,654,216 A    3/1987    Carroll et al.

FOREIGN PATENT DOCUMENTS

| EP | 0 132 289 | 1/1985 |
| EP | 0 171 995 | 2/1986 |
| WO | 91/04669 | 4/1991 |
| WO | 99/53769 | * 10/1999 |

OTHER PUBLICATIONS

Kweon et al., Journal of Food Science, vol. 59, No. 5, pp. 1072–1080 (1994).

* cited by examiner

*Primary Examiner*—Leslie Wong
(74) *Attorney, Agent, or Firm*—Elias J. Lambiris, Esq.; Jason I. Garbell, Esq.

(57) ABSTRACT

Disclosed is a process for preparing a dough or a baked product from the dough which process involves incorporating into the dough an anti-staling amylase and a phospholipase. The bread made by the combined use of an anti-staling amylase and a phospholipase has improved softness, both when eaten on the same day and when stored for several days after baking. There is no significant change in the taste or smell of the baked product.

12 Claims, No Drawings

PREPARATION OF DOUGH AND BAKED PRODUCTS

CROSS-REFERENCE TO RELATED APPLICATIONS

This application claims priority under 35 U.S.C. 119 of U.S. provisional application No. 60/083,277 filed Apr. 28, 1998 and Danish application no. 0543/98 filed Apr. 20, 1998, the contents of which are fully incorporated herein by reference.

FIELD OF THE INVENTION

The invention relates to process for preparing a dough or a baked product prepared from the dough. More particularly, it relates to such a process where the bread has an improved softness, both when eaten on the same day and when eaten after several days of storage.

BACKGROUND OF THE INVENTION

It is well known that the softness of bread deteriorates during storage from the time of baking to the time of consumption. The term staling is used to describe such undesirable changes in the properties of the bread. Staling results in an increase of the firmness of the crumb, a decrease of the elasticity of the crumb, and changes in the crust, which becomes tough and leathery.

Enzymatic retardation of staling by means of various amylases has been described. Thus, U.S. Pat. No. 2,615,810, U.S. Pat. No. 3,026,205 and O. Silberstein, "Heat-Stable Bacterial Alpha-Amylase in Baking", Baker's Digest 38(4), August 1964, pp. 66–70 and 72, describe the use of alpha-amylase. WO 91/04669 (Novo Nordisk) describes the use of a maltogenic alpha-amylase from *Bacillus stearothermophilus*. It is also known to use β-amylase to retard staling.

It is also known to add a phospholipase to dough. Thus, U.S. Pat. No. 4,567,046 and EP 171,995 (both to Kyowa Hakko) disclose that the addition of phospholipase A enhances the properties of dough and bread, including retardation of the staling.

M. R. Kweon et al., Journal of Food Science, 59 (5), 1072–1076 (1994) disclose the effect of 2–4% by weight of phospholipid hydrolysate together with an antistaling amylase on the retrogradation of starch in bread.

SUMMARY OF THE INVENTION

The inventors confirmed that the addition of an anti-staling amylase reduces the rate of crumb firming during storage for 1–7 days after baking, but they found that there is a need to improve the softness in the initial period after baking, particularly the first 24 hours after baking. They further found that this can be achieved by using a phospholipase, so that bread made by the combined use of an anti-staling amylase and a phospholipase has improved softness, both when eaten on the same day and when stored for several days after baking. There is no significant change in the taste or smell of the baked product.

Accordingly, the invention provides a process for preparing a dough or a baked product prepared from the dough which comprises adding to the dough an anti-staling amylase and a phospholipase. The invention also provides a dough and a pre-mix comprising these ingredients.

DETAILED DESCRIPTION OF THE INVENTION

Anti-staling Amylase

The anti-staling amylase used in the invention may be any amylase that is effective in retarding the staling (crumb firming) of baked products.

The amylase preferably has a temperature optimum in the presence of starch in the range of 30–90° C., preferably 50–80° C., particularly 55–75° C., e.g. 60–70° C. The temperature optimum may be measured in a 1% solution of soluble starch at pH 5.5.

The anti-staling amylase may be an endo-amylase, preferably a bacterial endo-amylase, e.g. from Bacillus. A preferred example is a maltogenic alpha-amylase (EC 3.2.1.133), e.g. from Bacillus. A maltogenic alpha-amylase from *B. stearothermophilus* strain NCIB 11837 its commercially available from Novo Nordisk A/S under the tradename Novamyl®. It is further described in U.S. Pat. No. 4,598,048 and U.S. Pat. No. 4,604,355 and in C. Christophersen et al., Starch, vol. 50, No. 1, 39–45 (1997).

Other examples of anti-staling endo-amylases are bacterial alpha-amylases, derived e.g. from Bacillus, particularly *B. licheniformis* or *B. amyloliquefaciens*.

The anti-staling amylase may be an exo-amylase such as β-amylase, e.g. from plant (e.g. soy bean) or from microbial sources (e.g. Bacillus).

The anti-staling amylase is added in an effective amount for retarding the staling (crumb firming) of the baked product. The amount of anti-staling amylase will typically be in the range of 0.01–10 mg of enzyme protein per kg of flour, e.g. 1–10 mg/kg. A maltogenic alpha-amylase is preferably added in an amount of 50–5000 MANU/kg of flour, e.g. 100–1000 MANU/kg. One MANU (Maltogenic Amylase Novo Unit) may be defined as the amount of enzyme required to release one Smog of maltose per minute at a concentration of 10 mg of maltotriose (Sigma M 8378) substrate per ml of 0.1 M citrate buffer, pH 5.0 at 37° C. for 30 minutes.

Phospholipase

The phospholipase may have $A_1$ or $A_2$ activity to remove fatty acid from the phospholipid and form a lyso-phospholipid. It may or may not have lipase activity, i.e. activity on triglycerides. The phospholipase preferably has a temperature optimum in the range of 30–90° C., e.g. 30–70° C.

The phospholipase may be of animal origin, e.g. from pancreas (e.g. bovine or porcine pancreas), snake venom or bee venom. Alternatively, the phospholipase may be of microbial origin, e.g. from filamentous fungi, yeast or bacteria, such as the genus or species Aspergillus, *A. niger*, Dictyostelium, *D. discoideum*, Mucor, *M. javanicus*, *M. mucedo*, *M. subtilissimus*, Neurospora, *N. crassa*, Rhizomucor, *R. pusillus*, Rhizopus, *R. arrhizus*, *R. japonicus*, *R. stolonifer*, Sclerotinia, *S. libertiana*, Trichophyton, *T. rubrum*, Whetzelinia, *W. sclerotiorum*, Bacillus, *B. megaterium*, *B. subtilis*, Citrobacter, *C. freundii*, Enterobacter, *E. aerogenes*, *E. cloacae* Edwardsiella, *E. tarda*, Etwinia, *E. herbicola*, Escherichia, *E. coli*, Klebsiella, *K. pneumoniae*, Proteus, *P. vulgaris*, Providencia, *P. stuartii*, Salmonella, *S. typhimurium*, Serratia, *S. liquefasciens*, *S. marcescens*, Shigella, *S. flexneri*, Streptomyces, *S. violeceoruber*, Yersinia, or *Y. enterocolitica*. A preferred phospholipase is derived from a strain of Fusarium, particularly *F. oxysporum*, e.g. from strain DSM 2672, as described in copending PCT/DK 97/00557.

The phospholipase is added in an amount which improves the softness of the bread during the initial period after baking, particularly the first 24 hours. The amount of phospholipase will typically be in the range of 0.01–10 mg of enzyme protein per kg of flour (e.g. 0.1–5 mg/kg) or 200–5000 LEU/kg of flour (e.g. 500–2000 LEU/kg).

A phospholipase with lipase activity is preferably added in an amount corresponding to a lipase activity of 20–1000

LU/kg of flour, particularly 50–500 LU/kg. One LU (Lipase Unit) is defined as the amount of enzyme required to release 1 μmol butyric acid per minute at 30.0° C.; pH 7.0; with Gum Arabic as emulsifier and tributyrin as substrate.

Phospholipase Activity (LEU)

In the LEU assay, the phospholipase activity is determined from the ability to hydrolyze lecithin at pH 8.0, 40° C. The hydrolysis reaction can be followed by titration with NaOH for a reaction time of 2 minutes. The phospholipase from porcine pancreas has an activity of 510 LEU/mg (taken as standard), and the phospholipase from *Fusarium oxysporum* has an activity of 1540 LEU/mg.

Phospholipid

The phospholipase may act on phospholipid provided by flour in the dough, so the separate addition of a phospholipid is not required. However, the softening effect may be increased by adding a phospholipid, preferably in an amount of 0.05–20 g/kg of flour, e.g. 0.1–10 g/kg. The phospholipid may be a diacyl-glycero-phospholipid, such as lecithin or cephalin.

Dough

The dough of the invention generally comprises wheat meal or wheat flour and/or other types of meal, flour or starch such as corn flour, corn starch, rye meal, rye flour, oat flour, oat meal, soy flour, sorghum meal, sorghum flour, potato meal, potato flour or potato starch.

The dough of the invention may be fresh, frozen or par-baked.

The dough of the invention is normally a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat (triglyceride) is added, and particularly to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyetliylene stearates, or lysolecithin, but the invention is particularly applicable to a dough which is made without addition of emulsifiers (other than optionally phospholipid).

Additional Enzyme

Optionally, an additional enzyme may be used together with the anti-staling amylase and the phospholipase. The additional enzyme may be a second amylase, such as an amyloglucosideise, a beta-amylase, a cyclodextrin glucandtransferase, or the additional enzyme may be a peptidase, in particular an exopeptidase, a transglutaminase, a lipase, a cellulase, a hemicellulase, in particular a pentosanase such as xylanase, a protease, a protein disulfide isomerase, e.g., a protein disulfide isomerase as disclosed in WO 95/00636, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipoxygenase, an L-amino acid oxidase or a carbohydrate oxidase.

The additional enzyme may be of any origin, including mammalian and plant, and preferably of microbial (bacterial, yeast or fungal) origin and may be obtained by techniques conventionally used in the art.

The xylanase is preferably of microbial origin, e.g. derived from a bacterium or fungus, such as a strain of Aspergillus, in particular of *A. aculeatus, A. niger* (cf. WO 91/19782), *A. awamori* (WO 91/18977), or *A. tubigensis* (WO 92/01793), from a strain of Trichoderma, e.g. *T. reesei*, or from a strain of Humicola, e.g. *H. insolens* (WO 92/17573, the contents of which is hereby incorporated by reference). Pentopan® and Novozym 384® (both from Novo Nordisk A/S) are commercially available xylanase preparations produced by *Trichoderma reesei*.

The amyloglucosidase may be an *A. niger* amyloglucosidase (such as AMG™, available from Novo Nordisk A/S, Denmark). Other useful amylase products include Grindamyl® A 1000 or A 5000 (available from Grindsted Products, Denmark) and Amylase® H or Amylase® P (available from Gist-Brocades, The Netherlands).

The glucose oxidase may be a fungal glucose oxidase, in particular an *Aspergillus niger* glucose oxidase (such as Gluzyme®, available from Novo Nordisk A/S, Denmark).

The protease may in, particular be Neutrase® (available from Novo Nordisk A/S, Denmark).

The lipase may be derived from a strain of Thernomyces (Humicola), Rhizomucor, Candida, Asperigillus, Rhizopus, or Pseudomonas, in particular from *Thermomyces lanuginosus (Humicola lanuginosa), Rhizomucor miehei, Candida antarcfica, Aspergillus niger, Rhizopus delemar* or *Rhizopus arrhizus* or *Pseudomonas cepacia*. In specific embodiments, the lipase may be Lipase A or Lipase B derived from *Candida antarctica* as described in WO 88/02775, or the lipase may be derived from *Rhizomucor miehei* as described in EP 238,023, or *Humicola lanuginosa* described in EP 305,216, or *Pseudomonas cepacia* as described in EP 214, 761 and WO 89/01032.

Baked Product

The process of the invention may be used for any kind of baked product prepared from dough, either of a soft or a crisp character, either of a white, light or dark type. Examples are bread (in particular white, whole-meal or rye bread), typically in the form of loaves or rolls, French baguette-type bread, pita bread, tortillas, cakes, pancakes, biscuits, cookies, pie crusts, crisp bread, steamed bread, pizza and the like.

Pre-mix

The present invention further relates to a pre-mix comprising flour together with an anti-staling amylase, a phospholipase and a phospholipid. The pre-mix may contain other dough-improving and/or bread-improving additives, e.g. any of the additives, including enzymes, mentioned above.

Enzyme Preparation

The invention provides an enzyme preparation comprising an anti-staling amylase and a phospholipase, for use as a baking additive in the process of the invention. The enzyme preparation is preferably in the form of a granulate or agglomerated powder. It preferably has a narrow particle size distribution with more than 95% (by weight) of the particles in the range from 25 to 500 μm.

Granulates and agglomerated powders may be prepared by conventional methods, e.g. by spraying the amylase onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

EXAMPLES

Example 1

Bread was baked with anti-staling amylase, phospholipase and phospholipid. As reference, bread was also baked without one or more of these ingredients.

The phospholipid was lecithin at a dosage of 10 g/kg. The phospholipase was from *Fusarium oxysporum* used at a dosage of 50, 250 or 500 LU/kg, corresponding to 0.04, 0.19 or 0.38 mg/kg. The anti-staling amylase was a maltogenic alpha-amylase from *B. stearothermophilus* (Novamyl) at a dosage of 750 MANU/kg (1 mg/kg). All dosages in the Examples were based on kg of flour.

Doughs were prepared according to a standard European straight dough procedure with 50 g yeast per kg of flour and 40 ppm of ascorbic acid. The doughs were scaled to 350 g and baked in lidded pans.

The crumb firmness was measured using a texture analyzer TA-XT2 from Stable Micro Systems. Texture was measured according to a modified ACCA method (American Cereal Chemists' Association). These measurements were made after 0 days (approximately 2 hours; after baking) and again after 1, 2 and 7 days storage (wrapped in double plastic bags and stored at 22° C.).

The results are shown as firmness versus additive and storage time:

| Additives | Phospholipase dosage (LU/kg) | 2 hours | 1 day | 2 days | 7 days |
|---|---|---|---|---|---|
| Invention: Anti-staling amylase + phospholipase + phospholipid | 50 | 316 | 417 | 517 | 868 |
| | 250 | 279 | 371 | 455 | 790 |
| | 500 | 248 | 324 | 410 | 752 |
| Reference: | | | | | |
| None (control) | 0 | 296 | 875 | 1207 | 2162 |
| Anti-staling amylase | 0 | 469 | 563 | 801 | 1083 |
| Phospholipid + phospholipase | 50 | 208 | 470 | 782 | 1560 |
| | 250 | 231 | 467 | 721 | 1424 |
| | 500 | 233 | 420 | 649 | 1303 |

Example 2

A baking test was made as in Example 1, but with dosages of 0.5 mg/kg of the phospholipase (770 LEU/kg) and 1 g/kg of the phospholipid. The results are given as firmness after storage, and for comparison the firmness is also expressed in % of the control.

| Additives | 2 hours | 5 hours | 12 hours | 20 hours | day 2 | day 3 |
|---|---|---|---|---|---|---|
| Invention: Anti-staling amylase + phospholipase + phospholipid | 181 (78%) | 195 (65%) | 223 (51%) | 241 (46%) | 277 (34%) | 303 (32%) |
| Reference: | | | | | | |
| None (control) | 233 (100%) | 302 (100%) | 434 (100%) | 526 (100%) | 824 (100%) | 959 (100%) |
| Anti-staling amylase | 372 (160%) | 468 (155%) | 518 (119%) | 482 (92%) | 547 (66%) | 637 (66%) |
| Phospholipid + phospholipase | 144 (62%) | 144 (47%) | 212 (49%) | 258 (49%) | 364 (44%) | 482 (50%) |

Example 3

A baking test was made as in Examples 1 and 2, using a different phospholipase. The phospholipase was from porcine pancreas at a dosage of 2 mg/kg (1020 LEU/mg). The dosages of the anti-staling amylase and the phospholipid were as in Example 2, and the results are presented as in Example 2:

| Additives | 2 hours | 5 hours | 12 hours | 20 hours | day 2 | day 3 |
|---|---|---|---|---|---|---|
| Invention: Anti-staling amylase + phospholipase + phospholipid | 342 (122%) | 411 (103%) | 420 (80%) | 431 (73%) | 485 (52%) | 559 (48%) |
| Reference: | | | | | | |
| None (control) | 281 (100%) | 398 (100%) | 524 (100%) | 588 (100%) | 937 (100%) | 1157 (100%) |

-continued

| Additives | 2 hours | 5 hours | 12 hours | 20 hours | day 2 | day 3 |
|---|---|---|---|---|---|---|
| Anti-staling amylase | 409 (146%) | 490 (123%) | 514 (98%) | 526 (89%) | 625 (67%) | 673 (58%) |
| Phospholipid + phospholipase | 218 (76%) | 260 (65%) | 367 (70%) | 472 (80%) | 668 (71%) | 906 (78%) |

The results of Examples 1–3 show that the addition of anti-staling amylase retards the crumb firming during storage, but increases the initial firmness compared to the control without additives. The addition of phospholipid+ phospholipase according to the invention is effective in avoiding the increased initial firmness and further reduces the rate of crumb firming during storage, compared to the anti-staling amylase alone.

Example 4

Bread loaves were baked with and without phospholipid (lecithin) as indicated below. The phospholipase was *F. oxysporum* used at a dosage of 1 mg/kg (1540 LEU/kg). The anti-staling amylase and the baking conditions were as described in Example 1. The results are given as firmness after storage:

| | Anti-staling amylase MANU/kg | Phospholipase mg/kg | Phospholipid g/kg | Firmness 2 hours | 1 day | 3 days |
|---|---|---|---|---|---|---|
| Control | 0 | 0 | 0 | 294 | 687 | 1179 |
| Invention | 750 | 1 | 10 | 200 | 229 | 277 |
| | 750 | 1 | 2 | 167 | 218 | 287 |
| | 750 | 1 | 1 | 167 | 232 | 305 |
| | 750 | 1 | 0.5 | 189 | 269 | 333 |
| | 750 | 1 | 0.1 | 196 | 260 | 381 |
| | 750 | 1 | 0 | 199 | 264 | 372 |

The results show that addition of anti-staling amylase and phospholipase clearly improves the softness, both initial softness (2 hours) and softness after storage (3 days). The softening effect can be further improved by addition of phospholipid. The optimum dosage appears to be about 1 mg/kg of phospholipid.

What is claimed is:

1. A process for preparing a dough or a baked product prepared from the dough, comprising adding to the dough an anti-staling maltogenic alpha-amylase in an amount effective for retarding the staling of the baked product and a phospholipase in an amount effective to improve the softness of the baked product prepared from the dough during the first 24 hours after baking.

2. The process of claim 1 wherein the anti-staling amylase has optimum activity in bread at 70–90° C.

3. The process of claim 1 wherein the phospholipase has a temperature optimum of 30–70° C.

4. The process of claim 1 wherein the phospholipase is of fungal origin.

5. The process of claim 1 which further comprises incorporating a phospholipid into the dough.

6. The process of claim 1 which does not comprise addition of fat.

7. The process of claim 1 which does not comprise addition of lysophospholipid.

8. The process of claim 1 which does not comprise addition of emulsifiers other than the phospholipid.

9. The process of claim 1 wherein the dough consists essentially of flour, water, yeast, salt and sugar.

10. The process of claim 1, wherein the maltogenic alpha-amylase is from *Bacillus stearothermophilus*.

11. A dough comprising an anti-staling maltogenic alpha-amylase in an amount effective for retarding the staling of a baked product and a phospholipase in an amount effective to improve the softness of the baked product prepared from the dough during the first 24 hours after baking.

12. A pre-mix for dough comprising flour, an anti-staling maltogenic alpha-amylase in an amount effective for retarding the staling of the baked product and a phospholipase in an amount effective to improve the softness of the baked product prepared from the pre-mix during the first 24 hours after baking.

\* \* \* \* \*

US006365204C1

(12) EX PARTE REEXAMINATION CERTIFICATE (6591st)
United States Patent
Spendler et al.

(10) Number: US 6,365,204 C1
(45) Certificate Issued: Dec. 30, 2008

(54) PREPARATION OF DOUGH AND BAKED PRODUCTS

(75) Inventors: Tina Spendler, Herlev (DK); Lone Nilsson, Binningen (CH); Claus Crone Fuglsang, Niva (DK)

(73) Assignee: Novozymes A/S, Bagsvaerd (DK)

Reexamination Request:
No. 90/010,088, Jan. 8, 2008

Reexamination Certificate for:
Patent No.: 6,365,204
Issued: Apr. 2, 2002
Appl. No.: 09/286,037
Filed: Apr. 5, 1999

Related U.S. Application Data
(60) Provisional application No. 60/083,277, filed on Apr. 28, 1998.

(30) Foreign Application Priority Data

Apr. 20, 1998 (DK) .................................. 0543/98

(51) Int. Cl.
*A21D 2/26* (2006.01)
*A21D 2/00* (2006.01)
*A21D 8/02* (2006.01)
*A21D 8/04* (2006.01)

(52) U.S. Cl. ........................ 426/28; 426/18; 426/19; 426/20; 426/549

(58) Field of Classification Search .................. None
See application file for complete search history.

(56) References Cited

U.S. PATENT DOCUMENTS

| | | |
|---|---|---|
| 5,716,654 A | 2/1998 | Groenendaal |
| 6,140,094 A | 10/2000 | Loffler et al. |
| 6,254,903 B1 | 7/2001 | Schuster et al. |
| 6,964,944 B1 | 11/2005 | Callisen et al. |
| 2005/0287250 A1 | 12/2005 | Olsen et al. |
| 2006/0075518 A1 | 4/2006 | Yaver et al. |
| 2008/0131951 A1 | 6/2008 | Bojsen |

FOREIGN PATENT DOCUMENTS

| | | |
|---|---|---|
| DK | 0543/98 | 4/1998 |
| EP | 0 120 693 A1 | 10/1984 |
| EP | 0130064 | 1/1985 |
| EP | 0214761 | 3/1987 |
| EP | 0109244 | 4/1987 |
| EP | 0 403 553 | 9/1989 |
| EP | 0 575 133 A2 | 12/1993 |
| EP | 0 869 167 A2 | 10/1998 |
| WO | 89/08403 A1 | 9/1989 |
| WO | 91/03565 A1 | 3/1991 |
| WO | 91/04669 | 4/1991 |
| WO | 94/04035 | 3/1994 |
| WO | 98/00029 A1 | 1/1998 |
| WO | 98/23162 | 6/1998 |
| WO | 98/26057 | 6/1998 |
| WO | 98/31790 | 7/1998 |
| WO | 01/39602 A1 | 6/2001 |
| WO | 04/018660 A2 | 3/2004 |

OTHER PUBLICATIONS

H. Outtrup and B.E. Norman, "Properties and Application of a Thermostable Maltogenic Amylase Produced by a Strain of*Bacillus* Modified by Recombinant–DNA Techniques", Starch/Stärke, vol. 36, No. 12, 1984, pp. 405–411.

Claus Christophersen et al., "Enzymatic Characterisation of Novamyl, a Thermostable alpha–Amylase", Starch/Stärke, vol. 50, No. 1, 1998, pp. 39–45.

S. Ohta & T. Torigoe, "70 Application of Enzymatic Modification of Phospho–Lipids on Breadmaking," Abstracts of AACC 68th Annual Meeting, Kansas City, MO, Oct. 30–Nov. 3, 1983.

S. Ohta et al., "Enzymatic Modification of Phospholipids for Gluten Improvement," First Int'l. Symposium, Enzymes in the Forefront of Food and Feed Industries, TKK, Espoo/Otaniemi, Finland, Jun. 15–17, 1988, pp. 1–13.

Joan Qi Si, "Even the freshest bread improves with Novamyl," BioTimes, vol. 14, No. 1, Mar. 1999, p. 3.

Byron S. Miller et al., "A Comparison of Cereal, Fungal, and Bacterial Alpha–Amylases as Supplements for Breadmaking," Food Technology, vol. 7, Jan. 1953, pp. 38–42.

Product technical sheet of Amylase P.

Keith R. Morgan et al., "Staling in Starch Breads: The Effect of Antistaling Alpha–Amylase," Starch/Stärke, vol. 49, No. 2, 1997, pp. 54–59.

Product sheet of the product Fermizyme® H of Gist Brocades, Apr. 1991.

Assay report of the product Fermizyme H of D19 submitted in the opposition proceedings against EP0585988 on Dec. 13, 1996.

Product sheet of Bakezyme P500 BG—Food Specialties, Revision 4, Nov. 3, 2004.

Exhibit 1—Determination of the MANU–value of Novamyl® 10,000 and Bakezyme® P500.

Exhibit 2—Effect of Novamyl® and fungal alpha–amylase on crumb firmness.

J.A. Gerrard et al, "The Role of Maltodextrins in the Staling of Bread," Journal of Cereal Science, vol. 26, 1997, pp. 201–209.

R.D. Dragsdorf & E. Varriano–Marston, "Bread Staling: X–Ray Diffraction Studies on Bread Supplemented with Alpha–Amylases from Different Sources", Cereal Chemistry, vol. 57, No. 5, 1980, pp. 310–314.

H.F. Zobel & F.R. Senti, "The Bread Staling Problem, X–Ray Diffraction Studies on Breads Containing a Cross–Linked Starch and a Heat–Stable Amylase," Cereal Chemistry, vol. 36, Sep. 1959, pp. 441–451.

(Continued)

*Primary Examiner*—Stephen J Stein

(57) ABSTRACT

Disclosed is a process for preparing a dough or a baked product from the dough which process involves incorporating into the dough an anti-staling amylase and a phospholipase. The bread made by the combined use of an anti-staling amylase and a phospholipase has improved softness, both when eaten on the same day and when stored for several days after baking. There is no significant change in the taste or smell of the baked product.

OTHER PUBLICATIONS

H.D. Seneviratne & C.G. Biliaderis, "Action of Alpha–Amylases on Amylose–lipid Complex Superstructures," Journal of Cereal Science, vol. 13, 1991, pp. 129–143.

Novo Nordisk Data Application Sheet—Novozym® 677 BG for Baking Bread.

Joan Qi Si & Cornelia Lustenberger, "Novamyl—A true Anti–Staling Enzyme," 1997. Based on oral presentation Oct. 1997. AACC Conference, San Diego.

Declaration of Jørn Borch Søe dated Sep. 7, 2006.

Novo Nordisk Product Sheet for Novozyme® 677 BG, Dec. 1995.

Ekozym Product Sheet for Lipopan 50BG.

C.H. Poulsen & J. Borch Søe, "Effect and Functionality of Lipases in Dough and Bread," The First European Symposium on Enzyme and Grain Processing, TNO Nutrition and Food Research Institute, 1997, pp. 204–214, ISBN 9075202040.

Statement of Danisco A/S in Civil Action No. 05–1972 (GEL)(DFE), pp. 47–48.

Declaration of Jørn Borch Soe dated Mar. 19, 2007.

Avanti Polar Lipids, Inc., Lipids by Extraction.

Experimental report by Henrik Lundqvist of Novazymes A/S entitled "Novamyl and phospholipase effect in starch bread" and dated Apr. 16, 2007.

K.J. Zeleznak & R.C. Hoseney, "The Role of Water in the Retrogradation of Wheat Starch Gels and Bread Crumb," Cereal Chemisty, vol. 63, No. 5, 1986, pp. 407–411.

Enzyme Nomenclature 1992, Academic Press, Inc., pp. 306, 307, 346, 347, 365, 604, 675.

Report by Henrik Lundqvist of Novozymes A/S entitled Phospholipase activity of Novozym 677 BG dated Aug. 28, 2007.

Enzyme Nomenclature for EC 3.2.1.1 at http://www.chem.qmul.ac.uk/iubmb/enzyme.

Sigma–Aldrich printout for Phospholipase $A_2$ from porcine pancreas.

Francis H.C. Tsao et al., "Multiple Forms of Porcine Pancreatic Phospholipase $A_2$: Isolation and Specificity," Journal of Supramolecular Structure, 1973, pp. 490–497.

Wiley Interscience printout showing publication date of C. Christophersen et al., article entitled "Enzymatic Characterisation of novamyl, a Thermostable Alpha–Amylase".

IUBMB Enzyme Nomenclature, EC 3.2.1.1, printed from http://www.chem.qmul.ac.uk/iubmb/enzyme Sep. 18, 2008.

IUBMB Enzyme Nomenclature, EC 3.2.1.33, printed from http://www.chem.qmul.ac.uk/iubmb/enzyme Sep. 18, 2008.

Kweon et al. Phospholipid hydrolysate and antistaling amylase effects on retrogradation of starch in bread. Journal of Food Science 59(5): 1072–1076, 1994.

Si and Lustenberger. Novamyl®—a true anti–staling enzyme A–06565. Novo Nordisk. A presentation published at IFIA in Japan and at the meeting at IATA in Valencia, Spain, May 1998.

Si. "Synergistic effect of enzymes for breadbaking", Cereal Foods World 42(10): 802–807, 1997.

Enzyme catalyzed synthesis of structured phospholipids with conjugated linoleic acid and plant sterols. A Dissertation by MD.Monjur Hossen. May 2005.

Mustranta et al., "Comparison of lipases and phospholipases in the hydrolysis of phospholipids," Process Biochemistry 30(5):393–401, 1995.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 is confirmed.

* * * * *

(12) EX PARTE REEXAMINATION CERTIFICATE (7684th)
United States Patent
Spendler et al.

(10) Number: US 6,365,204 C2
(45) Certificate Issued: Aug. 10, 2010

(54) PREPARATION OF DOUGH AND BAKED PRODUCTS

(75) Inventors: Tina Spendler, Herlev (DK); Lone Nilsson, Binningen (CH); Claus Crone Fuglsang, Niva (DK)

(73) Assignee: Novozymes A/S, Bagsvaerd (DK)

Reexamination Request:
No. 90/010,517, Apr. 30, 2009

Reexamination Certificate for:
Patent No.: 6,365,204
Issued: Apr. 2, 2002
Appl. No.: 09/286,037
Filed: Apr. 5, 1999

Reexamination Certificate C1 6,365,204 issued Dec. 30, 2008

Related U.S. Application Data
(60) Provisional application No. 60/083,277, filed on Apr. 28, 1998.

(30) Foreign Application Priority Data

Apr. 20, 1998 (DK) ................................................ 054398

(51) Int. Cl.
*A21D 2/26* (2006.01)
*A21D 2/00* (2006.01)
*A21D 8/02* (2006.01)
*A21D 8/04* (2006.01)

(52) U.S. Cl. .............................. 426/28; 426/18; 426/19; 426/20; 426/549

(58) Field of Classification Search ........................ None
See application file for complete search history.

(56) References Cited

U.S. PATENT DOCUMENTS

| | | | |
|---|---|---|---|
| 2,615,810 A | 10/1952 | Stone | |
| 3,026,205 A | 3/1962 | Stone | |
| 4,567,046 A | 1/1986 | Inoue et al. | |
| 4,598,048 A * | 7/1986 | Diderichsen et al. | ..... 435/91.41 |
| 6,197,352 B1 | 3/2001 | Olesen | |

OTHER PUBLICATIONS

Eliasson, et al., *Cereals in Breadmaking: A Molecular Colloidal Approach,* Marcel Dekkar, Inc., New York, NY, 1993, pp. 310–314.
Carlson et al., "Phase Equilibria and Structures in the Aqueous of Wheat Lipids" *Cereal Chem.* 55(2): 168–179 (1978).
Carlson et al., "Phase Equilibria in the Aqueous of Wheat Lipids and in the Aqueous Salt System of Wheat Lipids," *Cereal Chem.* 56(5): 417–419 (1979).
Frank, P., "Fresh-keeping technology builds brand equity," *Baking Management,* Nov. 2008, pp. 28–33.
Eliasson, Ann-Charlotte et al., *Cereals in Breadmaking: A Molecular Colloidal Approach,* Marcel Dekker, Inc., NY 1993, pp. 33, 36.
Morrison, W. R., Cereal Chem. 55(5), 548–558 (1978).
Silverstein, O., "Heat Stable Bacterial Alpha-Amylase in Baking: Application to White Bread," *The Bakers Digest,* Aug. 1964, pp. 66–70, 72.

* cited by examiner

*Primary Examiner*—Bruce Campell

(57) ABSTRACT

Disclosed is a process for preparing a dough or a baked product from the dough which process involves incorporating into the dough an anti-staling amylase and a phospholipase. The bread made by the combined use of an anti-staling amylase and a phospholipase has improved softness, both when eaten on the same day and when stored for several days after baking. There is no significant change in the taste or smell of the baked product.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

\* \* \* \* \*